United States Patent
Lunn

Patent Number: 5,876,433
Date of Patent: Mar. 2, 1999

[54] STENT AND METHOD OF VARYING AMOUNTS OF HEPARIN COATED THEREON TO CONTROL TREATMENT

[75] Inventor: Anthony C. Lunn, Princeton, N.J.

[73] Assignee: Ethicon, Inc., Somerville, N.J.

[21] Appl. No.: 654,948

[22] Filed: May 29, 1996

[51] Int. Cl.$^6$ .................................................. A61M 29/02
[52] U.S. Cl. ................................. 623/1; 623/12; 606/198
[58] Field of Search ..................................... 606/198, 191; 623/1, 12

[56] References Cited

U.S. PATENT DOCUMENTS 5,554,182  9/1996  Dinh et al. ........................... 606/194 X

*Primary Examiner*—Michael H. Thaler
*Attorney, Agent, or Firm*—Paul A. Coletti

[57] ABSTRACT

The present invention addresses two previously unresolved problems simultaneously. First, the question concerning the amount of heparin applied to a stent is resolved. That is, the invention set forth herein will demonstrate that by varying the amount of heparin, the practitioner can actually more adequately determine whether in fact the patient will receive the correct dosage to address the problem, and at the right time in which to address the problem. Second, the problem of applying the heparin coating to a stent is addressed. There, specifically, the invention turns to the fashion in which to apply multiple layers of heparin coating to the stent, and to thereby variably adjust the dosage applied to the patient at the lesion site. The present invention does so by providing a method and device for coating a stent with multiple layers of heparin coating. By so doing, the heparin coating is absorbed by the body in a degree which varies with the amount of heparin applied. Thus, contrary to formerly popular belief, the present method allows for the significant adjustment of heparin therapy. And, the stent so coated allows for the variable application of such heparin therapy at the lesion site.

8 Claims, 3 Drawing Sheets

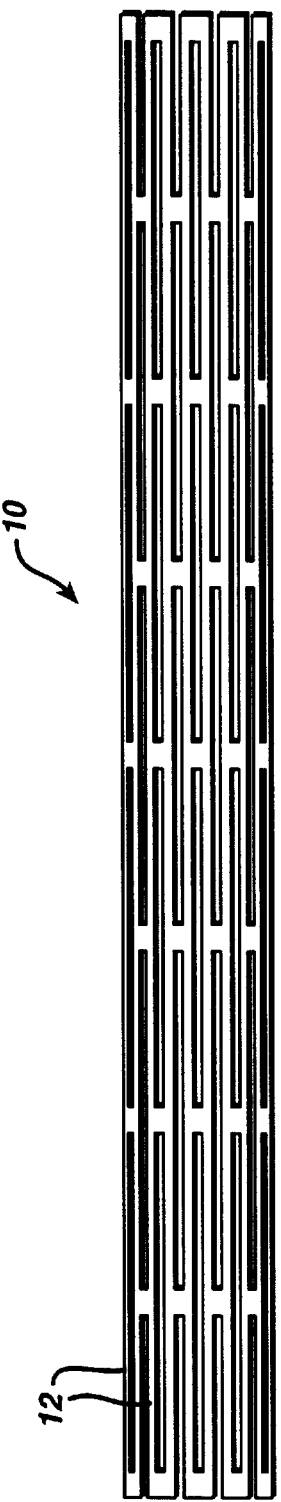

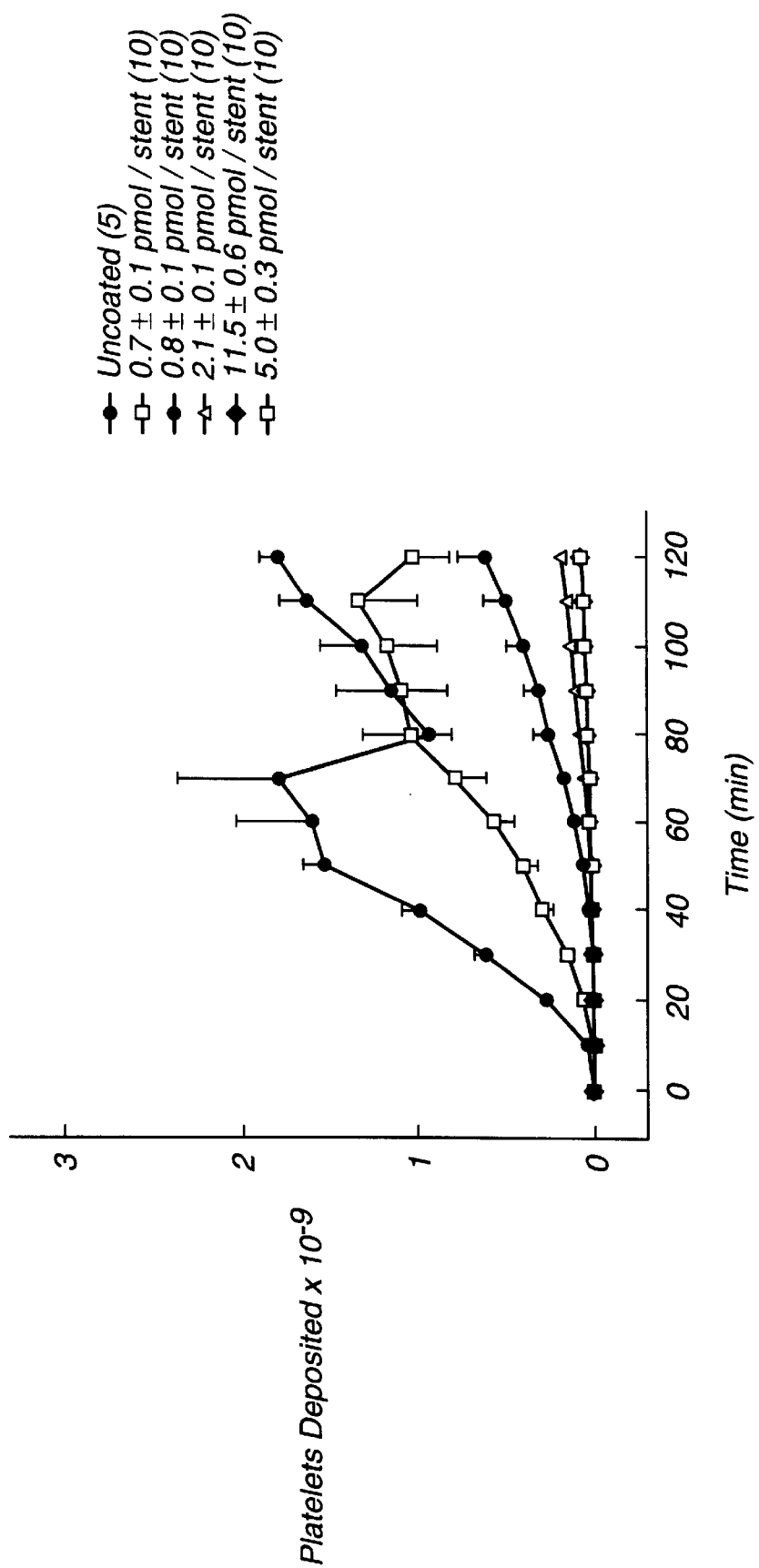

STENT AND METHOD OF VARYING AMOUNTS OF HEPARIN COATED THEREON TO CONTROL TREATMENT

FIELD OF THE INVENTION

Briefly, this invention relates to coating stents with heparin or other anti-coagulant treatments. More specifically, this invention relates to varying the amount and activity of heparin coated on a stent in order to improve the efficacy at the lesion site, upon deployment of the stent.

BACKGROUND OF THE INVENTION

The use of stents to hold open the lumens of blood vessels has become quite widespread. The Palmaz-Schatz stent marketed by Johnson & Johnson Interventional Systems of Warren N.J. has become universally recognized as the premier device for holding open occluded blood vessels, including the occluded coronary arteries. Nonetheless, the use of these stents is limited to a certain degree. That is, it is not always possible to prevent thrombosis arising near the lesion site, and there is always the possibility of occlusion of the lumen in the days following stent implantation. It would be desirable to provide the patient with protection against such undesirable events. This therapy, it is believed, helps to prevent early thrombus. Also, it appears that the heparin treatment will help to reduce the occurrence and the degree of restenosis.

With this in mind, there is a need for technology which will enable the interventionalist to apply heparin or other therapy to the surface of an implanted device in optimum degrees, But, the theory about such treatment has heretofore been an all or nothing approach. Simply, the interventionist believed that the amount of heparin applied and the nature of its attachment would not matter. There could be no middle ground. As this mindset set in, there simply would be no attention paid to researching the way to apply varying amounts of heparin, and, for that matter, whether the varying amounts of heparin on the stent actually could matter.

SUMMARY OF THE INVENTION

Accordingly, the present invention addresses two previously unresolved problems simultaneously. First, the question concerning the amount of heparin applied to a stent is resolved. That is, the invention set forth herein will demonstrate that by varying the amount of heparin, the thromboresistance of the surface can be significantly altered. Second, the problem of applying the heparin coating to a stent will be addressed. There, specifically, the invention turns to the fashion in which to apply controlled quantities and multiple layers of heparin coating to the stent, and to thereby variably adjust the dosage applied to the patient at the lesion site.

The present invention does so by providing a method and device for coating a stent with heparin coatings with variable levels of antithrombin III activity. By so doing, the thromboresistance of the heparin coating can be optimized. Thus, contrary to formerly popular belief, the present method allows for the significant adjustment of heparin therapy. And, the stent so coated allows for the improved application of such heparin therapy at the lesion site, based on the bio-activity at the site due to the antithrombin III uptake at the lesion site.

DESCRIPTION OF THE DRAWINGS

The present invention will be more readily understood in combination with the appended figures, taken in combination with a detailed description of the invention, wherein:

FIGS. 1 and 1a are a perspective views of a heparin coated stent as seen in unexpanded and balloon expanded conditions, respectively; and FIG. 2 is a graph charting results of tests performed using various layers and molecularities of heparin as coated on stents.

DETAILED DESCRIPTION OF THE INVENTION

Figure 1A:
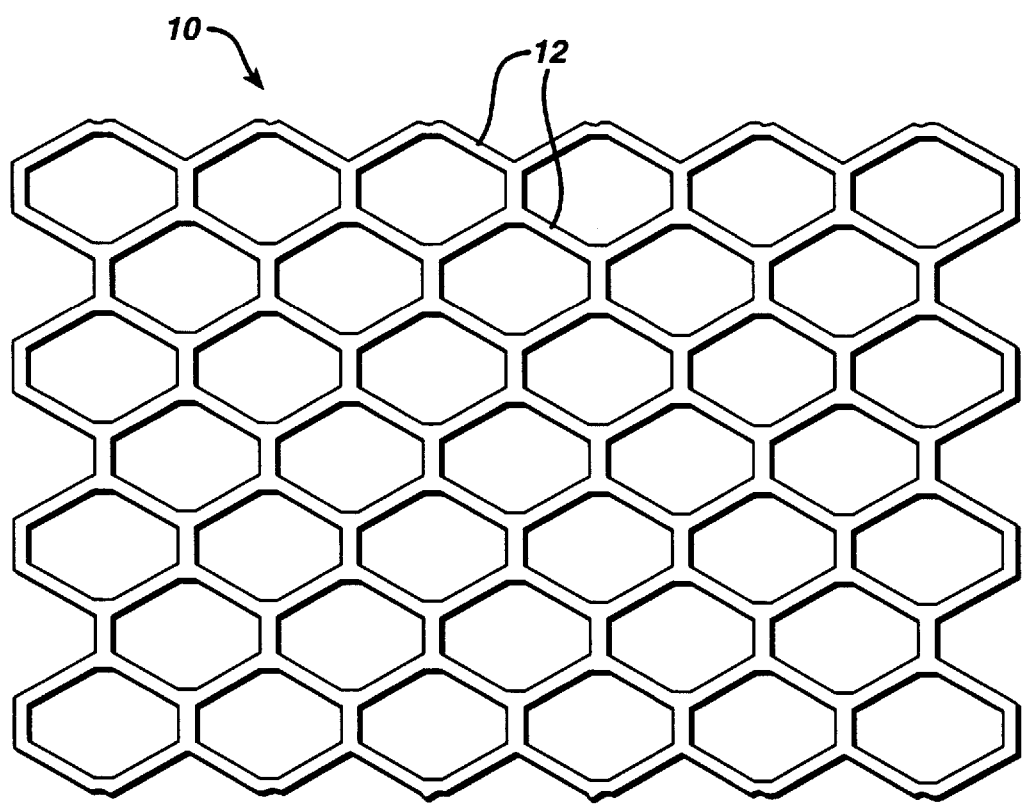

As seen in FIGS. 1 and 1a, there is described a balloon expandable stent 10. This stent is ideally the Palmaz-Schatz stent made and sold by Johnson & Johnson Interventional Systems of Warren N.J. This stent 10 is typically formed from a polished metal, and typically contains no burrs or irregularities on its surface. In use, as is well known by now in the art, the typical stent (having a surface area of 0.8 $cm^2$) is uncoated with any surface treatment, unlike the stent 10 of FIG. 1. The stent 10 is placed on a steerable balloon angioplasty catheter, not shown, and guided through the arterial vasculature to a lesion situs. Once the guidewire of the catheter has crossed the lesion, the balloon with stent attached is put in place, itself traversing the lesion. Then, the balloon is expanded.

Upon expansion, the walls of the balloon open, and thereby force the walls 12 of the stent 10 to expand, as seen in FIG. 1a. The balloon forces the material from which the stent is made to expand deformably, beyond the elastic limit of the material. The stent then takes on the shape as seen in FIG. 1a, again without the coating applied. This causes the material to take a permanent set, and thereby "plastically" deform. The resultant shape of the stent is quite rigid, allowing the stent to hold open the walls of the artery at the lesion, thus restoring patency to the vessel.

Heretofore it has been suggested by many that the walls 12 of the stent 10 may desirably be coated with anti-thrombogenic agents, such as heparin. Thus, the assignee of the current invention has embarked on a study to coat the walls 12 of a Palmaz-Schatz stent 10 with heparin. One desirable method used is that method and apparatus described in, among other things, the patents assigned to Carmeda A B, notably, U.S. Pat. Nos. 4,565,740; 4,613,665; 4,810,784; 5,049,403; and 5,213,898, incorporated herein by reference. With a heparin coating of any sort, the bioavailability of antithrombin III on the surface appears to increase the possibility of reducing thrombus, especially in the first one or two hours after the placement of a stent 10. Nonetheless, as explained before, the amount and activity of heparin applied to the stent has never been taken to matter. The applicant herein has discovered a truly unexpected result, as a byproduct of the following experimental data.

EXAMPLE

To assess the extent of platelet deposition on a non-coated and Carmeda heparin coated endovascular (JJIS) stent placed in a baboon (*Papio cynocephalus*) ex-vivo arterio-venous shunt model. Initially the Carmeda heparin coating (CH5) was compared to the non-coated (control) stent. The CH5 coating was shown to be highly thromboresistant as compared to the thrombogenic non-coated stent JJIS Coronary Stent. Platelet deposition was measured on the coronary stent placed in the silicone shunt tubing and exposed to non-anticoagulated flowing blood for 2 hour in the ex-vivo arteriovenous shunt. In subsequent studies the level of Antithrombin III uptake activity on the stent surface was altered to allow for characterization of the influence of heparin activity on the stent surface in the inhibition of platelet deposition and thrombus formation on the endovascular stent. This model for measuring platelet deposition at the site of stent placement in an ex-vivo primate shunt using radiolabeled platelets was developed at Emory University, whose aid in proving the efficacy of the present invention is noted with appreciation. The following protocol describes the measurement of platelet deposition after stent placement in this model.

Materials:

Ultrasonic flowmeter (Model 201, Transonics Systems, Ithaca, N.Y.).—flow maintained at 100 mls/min.
Gamma Scintillation Camera (General Electric 400T MaxiCamera, Milwaukee, Wis.).
Computer-assisted image processing system interfaced with the camera (Medical Data Systems $A^3$, Medtronic Inc., Minneapolis, Minn.).
3.5 mm JJIS Coronary Stents
Automated Platelet Counter
Whole Blood Analyzer
Indium oxide
Autologous Fibrinogen $^{125}$I
A-V shunt in baboon (*Papio cynocephalus*)

Methods:

Normal male baboons (*Papio cynocephalus*) were used in these experiments. All studies were approved by the Institutional Animal Care and Use Committee and were performed in accordance with federal guidelines (Guide for the Care and Use of Laboratory Animals, NH Publication No. 86-23). The animals weigh 10 to 12 kg and were quarantined and observed to be disease-free for 3 months before use. All animals had a chronic arteriovenous shunt surgically implanted between the femoral artery and vein. Ketamine hydrochloride 10 mg/ml was used as a preanesthetic agent, and the shunt placement operation was performed after the animals were anesthetized with halothane. The permanent shunt system consisted of two 2.5 cm lengths of polydimethyl siloxane (Silastic, Dow Corning, Midland, Mich.) tubing, 3.0 mm inside diameter (i.d.) Blood flow was established by connecting the two Silastic shunt segments with a 2 cm length of polytetrafluoroethylene (Teflon) tubing 2, 8 mm i.d.). As described in detail in the literature, the permanent Teflon-Silastic shunts do not detectably shorten platelet survival or produce measurable platelet activation.

Platelet count and hematocrit determinations were performed on whole blood collected in EDTA at 2 mg/ml by using a whole-blood analyzer. Mean blood flow rates through the stented segments incorporated into the arteriovenous shunt system were measured continuously by using an ultrasonic flowmeter with a transducer probe placed around the Silastic tubing constituting the shunt. In all studies the flow rates were maintained at 100 ml/min (wall shear rate 265 $sec^{-1}$, a flow rate typical of medium-sized coronary arteries). Stents were placed and imaged after the re-injection of autologous $^{111}$indium labeled platelets. The stents were imaged for 2 hours and then removed from the shunt and flushed and fixed in 2.5% buffered glutaraldehyde for subsequent surface analysis.

Platelet Labeling:

Autologous baboon platelets were labeled with $^{111}$Indium-oxine as previously described. One hundred milliliters of whole blood was collected directly into two conical tubes each containing 10 ml of acid-citrate-dextrose anticoagulant. The blood was centrifuged at 300 g for 10 minutes. The supernatant platelet rich plasma (PRP) was transferred to a second conical tube and the pH adjusted to 6.5 by the addition of 0.15 mol.L citric acid (0.1 ml per 10 ml PRP). The erythrocyte fraction was returned to the donor animal. The platelets were formed into a pellet by centrifugation of the PRP at 1300 g for 15 minutes. The platelet-poor supernatant was completely decanted and discarded. To remove residual plasma proteins, the platelet pellet was carefully washed with 30 ml of Ringer's citrate dextrose (pH 6.5), which was decanted and discarded. The platelet pellet was then gently resuspended in 5.0 ml of RCD and incubated for 10 min. with 800–1000 mCi (1 ci=37 GBq) of $^{111}$In-oxine (Amersham, Arlington Heights, Ill.). Contaminating erythrocytes were removed by a final slow centrifugation at 200 g for 5 minutes. This labeling technique achieves a labeling efficiency of >90%. The labeled platelets were then re-injected to the donor baboon thus labeling the circulating platelet pool. The platelets were re-injected at least 1 hour prior to the shunt study to allow time for redistribution within the circulating pool.

Imaging:

Gamma camera images of the stents, including proximal and distal Silastic segments was acquired with a gamma camera (400T MaxiCamera, General Electric, Milwaukee, Wis.) and stored on and analyzed by a computer (Medical Data Systems $A^3$ Medtronic, Ann Arbor, Mich.), interfaced with the gamma camera. A defined region of the silastic tubing proximal to the stented segment was used as the control (blood standard). The activities of the standard and 1.5 cm stent segments were measured in the same 3×6 cm (10×20 pixels) region of interest as defined by image analysis software routines. Images of the 15% energy window ($^{111}$In peak) were acquired at 5-minute intervals in 128×128 byte mode. The total number of platelets deposited at each time point (labeled and unlabeled cells) was calculated by dividing the deposited platelet activity by the blood standard platelet activity and multiplying by the volume of the blood standard and the circulating platelet count (platelets per milliliter).

Stent Deployments in Silicone Tubing:

Single stainless steel metal Palmaz-Schatz™ slotted tube stents uncoated (Control) or heparin-coated were deployed, using a standard 3.5 mm diameter 20 mm long non compliant angioplasty balloon inflated 3 times to 10 atmospheres, into 30 cm segments of silicone rubber tubing (3.2 mm i.d.). The stents diameter was eventually 3.5 mm, as previously measured by intravascular ultrasound (IVUS) in shunt tubing. The stents were well opposed by the high pressure balloon inflation against the side of the tubing. The stents were deployed at least 10 cm from the end of the tube to avoid any connector artifact. At the time of the shunt study the stented segment of the silicone tubing was attached to the Silastic tubing comprising the chronic arteriovenous shunt with 2 cm-long tapered Teflon connectors. After exposure to flowing blood, the silicone tubing segment containing the stent was removed, placed in buffered 2.5% glutaraldehyde fixative for 10 minutes and then transferred to cacodylate buffer, and stored at 4° C.

Results

When the JJIS Palmaz-Schatz coronary stent is coated with the Carmeda CH5 Heparin coating, there is a substantial reduction in platelet deposition during the period of the exposure of the stent to flowing non-anticoagulated blood in the AV-shunt. It is also clear that the suppression of platelet deposition varies significantly with the level of antithrombin-III activity in the heparin coating on the stent surface. As seen in FIG. 2, as the antithrombin-III activity increases from 0.7 to 0.8 to 2.1 to 5.0 picomoles per stent, the suppression of platelet deposition is enhanced. (The data at 11.5 pmol/stent are almost coincident with the 5.0 pmol/stent data, so their data points are not readily seen in the graph.) It is worth noting that some samples of the non-coated stent began to embolize platelet rich material at times after 45 minutes. This explains the drop in platelet deposition as shown graphically after 60 minutes. Any statistical comparison would thus be relevant only to 45 minutes as there is a falsely low platelet deposition on the control stent after this chronological point in the sampling data.

These results are highly significant. These heparin coatings appear highly effective in inhibiting thrombus formation in this highly thrombotic model of the stent placed in the ex vivo AV shunt.

As seen from FIG. 2 and Table I below, there is indeed a relationship between the amount and activity of heparin initially coated on the stent, and the reduction of thrombus at the lesion sites. This relationship appears to the applicant to be wholly inversely proportional upon the amount of heparin activity on the stent. In other words, the more heparin coated, the less thrombogenic the stent when emplaced at a lesion and expanded beyond its elastic limit. Of course, these results are directly in contrast to the published expected results hypothesized by those skilled in the art.

TABLE I

| AT - III Activity (pmol/stent) | Heparin Level (Micrograms /Stent) |
|---|---|
| 0.7 ± 0.1 | 0.26 ± 0.08 |
| 0.8 ± 0.1 | 0.50 ± 0.08 |
| 2.1 ± 0.1 | 1.42 ± 0.08 |
| 5.0 ± 0.3 | 4.4 ± 0.2 |
| 11.5 ± 0.6 | 7.9 ± 0.2 |

The merits of such a study are quite apparent. It is perceived that, armed with knowledge of this data, the interventionalist can tailor the amount of heparin treatment to the patient; conversely, in production, the manufacturer can tailor the stents according to the perceived amount of heparin treatment needed by patients in the marketplace. In either event, the patients are more adequately served by the progress achieved in this invention. Accordingly, therefore, these unexpected results are meritorious of patentability, which is to be determined from the following appended claims and their equivalents.

What is claimed is:

1. A stent for placement in a lumen of the body, and said stent placed into said lumen so as to contact said lumen, said stent coated with heparin wherein the stent is coated with enough heparin to insure above 0.7 pmol/cm$^2$ antithrombin III is absorbed by the body when the lumen contacts said stent.

2. A stent according to claim 1 wherein the stent is coated with a plurality of layers of variable density of said heparin coating.

3. A method of placing the stent of claim 1 comprising the steps of:

determining the lesion site in said lumen to which the stent is to be employed;

predetermining the amount of heparin needed on a said stent at said lesion site in order to insure above 0.7 pmol/cm$^2$ of antithrombin II is absorbed by the body with where the lesion contacts said stent;

coating said stent with the predetermined amount of said heparin; and emplacing said stent into the body at said lesion site.

4. A stent of claim 1 wherein the stent is coated with enough heparin to insure the uptake of at least 10 pmol per cm$^2$ of antithrombin III.

5. A method of placing a stent coated with heparin wherein the amount of heparin is variably adjusted depending on the desired use of the said stent comprising the steps of:

determining the lesion site to which the stent is to be employed;

predetermining the amount of heparin needed on a said stent at said lesion site;

coating said stent with the predetermined amount of said heparin wherein the stent is coated with enough heparin to insure at least 0.7 pmol/cm$^2$ uptake of antithrombin III is absorbed by the body at said lesion site.

6. A method according to claim 5 wherein the stent is coated with a plurality of layers of variable density of said heparin coating.

7. A method according to claim 5 wherein the stent is useful for a particular lesion site in the body, said lesion site affecting the level of heparin coated on said stent.

8. A method according to claim 5 wherein the stent is coated with enough heparin to insure the uptake of at least 10 pmol per cm$^2$ of antithrombin III.

* * * * *